US009080938B2

(12) United States Patent
Cai et al.

(10) Patent No.: US 9,080,938 B2
(45) Date of Patent: Jul. 14, 2015

(54) EXTREMUM SEEKING ALGORITHM IN A VARIABLE TIME INTERVAL TO DETECT ANODE PRESSURE SENSOR STUCK FAILURE IN A FUEL CELL SYSTEM

(75) Inventors: Jun Cai, Fairport, NY (US); Daniel C. Di Fiore, Scottsburg, NY (US); Steven R. Falta, Honeoye Falls, NY (US); Sergio E. Garcia, Webster, NY (US); Carol A. Galskoy, Webster, NY (US)

(73) Assignee: GM Global Technology Operations LLC, Detroit, MI (US)

( * ) Notice: Subject to any disclaimer, the term of this patent is extended or adjusted under 35 U.S.C. 154(b) by 286 days.

(21) Appl. No.: 13/560,352

(22) Filed: Jul. 27, 2012

(65) Prior Publication Data

US 2014/0026633 A1 Jan. 30, 2014

(51) Int. Cl.
*G01L 27/00* (2006.01)
*H01M 8/04* (2006.01)
*G01N 27/00* (2006.01)

(52) U.S. Cl.
CPC ......... *G01N 27/007* (2013.01); *H01M 8/04388* (2013.01); *H01M 8/04402* (2013.01); *H01M 8/04425* (2013.01); *H01M 8/04664* (2013.01); *H01M 8/04686* (2013.01); *H01M 8/04* (2013.01); *H01M 8/0438* (2013.01); *H01M 8/04649* (2013.01); *H01M 8/04753* (2013.01); *Y02E 60/50* (2013.01)

(58) Field of Classification Search
CPC .... G01L 27/007; H01M 8/04; H01M 8/0438; H01M 8/04402; H01M 8/04425; H01M 8/04432; H01M 8/04664; H01M 8/04686; H01M 8/04388; Y02E 60/50

USPC ................... 73/1.59, 1.63–1.64; 429/61, 90; 701/30.5, 30.8–31.3, 34.4, 36, 701/FOR. 105; 702/98, 116
See application file for complete search history.

(56) References Cited

U.S. PATENT DOCUMENTS

| | | | | |
|---|---|---|---|---|
| 3,573,988 A | * | 4/1971 | McKee et al. ........... | Y02E 60/50 |
| 7,320,840 B2 | * | 1/2008 | Pechtold et al. ........ | H01M 8/04 |
| 8,679,691 B2 | * | 3/2014 | Lang et al. ........ | H01M 8/04686 |
| 2007/0218327 A1 | * | 9/2007 | Ishikawa et al. .. | H01M 8/04686 |
| 2008/0206607 A1 | * | 8/2008 | Mallavarapu et al. .. | H01M 8/04 |

(Continued)

FOREIGN PATENT DOCUMENTS

| | | | | | |
|---|---|---|---|---|---|
| JP | 2008177116 A | * | 7/2008 | ............. | H01M 8/04 |
| JP | 2012142145 A | * | 7/2012 | ............. | H01M 8/04 |
| WO | WO 2006048983 A1 | * | 5/2006 | ............. | H01M 8/04 |

*Primary Examiner* — Thomas P Noland
(74) *Attorney, Agent, or Firm* — John A. Miller; Miller IP Group, PLC

(57) ABSTRACT

A system and method for detecting an anode pressure sensor failure in a fuel cell system. The system and method include a controller that sets an initial minimum anode pressure sensor value and an initial maximum anode pressure sensor value. The controller determines a desired time interval for sampling anode pressure measurements and determines a total number of samples of anode pressure measurements to be collected by the controller from an anode pressure sensor. The controller also compares a pressure difference between the initial or a measured minimum anode pressure and the initial or a measured maximum anode pressure to a predetermined pressure difference threshold and sets a pressure sensor fault if the pressure difference between the initial or measured minimum anode pressure and the initial or maximum anode pressure is less than the predetermined pressure difference threshold.

20 Claims, 3 Drawing Sheets

(56) References Cited

U.S. PATENT DOCUMENTS

| | | | |
|---|---|---|---|
| 2009/0035630 A1* | 2/2009 | Kumada et al. | H01M 8/04 |
| 2010/0190079 A1* | 7/2010 | Devries et al. | H01M 8/04 |
| 2011/0143243 A1* | 6/2011 | Arthur et al. | Y02E 60/50 |
| 2011/0236780 A1* | 9/2011 | Furusawa et al. | H01M 8/04 |
| 2015/0004511 A1* | 1/2015 | Cauchi et al. | H01M 8/04 |
| 2015/0004512 A1* | 1/2015 | Ikezoe et al. | H01M 8/04 |

* cited by examiner

EXTREMUM SEEKING ALGORITHM IN A VARIABLE TIME INTERVAL TO DETECT ANODE PRESSURE SENSOR STUCK FAILURE IN A FUEL CELL SYSTEM

BACKGROUND OF THE INVENTION

1. Field of the Invention

This invention relates generally to a process for detecting an anode pressure sensor failure in a fuel cell system and, more particularly, to a process for determining maximum and minimum anode pressure sensor readings over a period of time to determine if a threshold difference between the minimum and maximum pressure has been achieved to determine if there is an anode pressure sensor stuck failure.

2. Discussion of the Related Art

Hydrogen is a very attractive fuel because it is clean and can be used to efficiently produce electricity in a fuel cell. A hydrogen fuel cell is an electro-chemical device that includes an anode and a cathode with an electrolyte therebetween. The anode receives hydrogen gas and the cathode receives oxygen or air. The hydrogen gas is dissociated in the anode to generate free hydrogen protons and electrons. The hydrogen protons pass through the electrolyte to the cathode. The hydrogen protons react with the oxygen and the electrons in the cathode to generate water. The electrons from the anode cannot pass through the electrolyte, and thus are directed through a load to perform work before being sent to the cathode.

Proton exchange membrane fuel cells (PEMFC) are a popular fuel cell for vehicles. The PEMFC generally includes a solid polymer electrolyte proton conducting membrane, such as a perfluorosulfonic acid membrane. The anode and cathode typically include finely divided catalytic particles, usually platinum (Pt), supported on carbon particles and mixed with an ionomer. The catalytic mixture is deposited on opposing sides of the membrane. The combination of the anode catalytic mixture, the cathode catalytic mixture and the membrane define a membrane electrode assembly (MEA). MEAs are relatively expensive to manufacture and require certain conditions for effective operation.

Several fuel cells are typically combined in a fuel cell stack to generate the desired power. For example, a typical fuel cell stack for a vehicle may have two hundred or more stacked fuel cells. The fuel cell stack receives a cathode input gas, typically a flow of air forced through the stack by a compressor. Not all of the oxygen is consumed by the stack and some of the air is output as a cathode exhaust gas that may include water as a stack by-product. The fuel cell stack also receives an anode hydrogen input gas that flows into the anode side of the stack.

The fuel cell stack includes a series of bipolar plates positioned between the several MEAs in the stack, where the bipolar plates and the MEAs are positioned between two end plates. The bipolar plates include an anode side and a cathode side for adjacent fuel cells in the stack. Anode gas flow channels are provided on the anode side of the bipolar plates that allow the anode reactant gas to flow to the respective MEA. Cathode gas flow channels are provided on the cathode side of the bipolar plates that allow the cathode reactant gas to flow to the respective MEA. One end plate includes anode gas flow channels, and the other end plate includes cathode gas flow channels. The bipolar plates and end plates are made of a conductive material, such as stainless steel or a conductive composite. The end plates conduct the electricity generated by the fuel cells out of the stack. The bipolar plates also include flow channels through which a cooling fluid flows.

Pressure sensors are an important piece of hardware for engine control in the automotive industry in general. There are diagnostics that cover a map sensor and a fuel pressure sensor for an internal combustion engine, where the fuel pressure sensor reading is compared to an estimated/model value and a trigger is set when the model and the sensor differ by a calibrated value. In fuel cell systems, pressure sensors are used for pressure control, emission control, valve control, etc. If one of the pressure sensor failures in a fuel cell system is due to a pressure sensor that is stuck at a pressure reading, the sensor will provide a flat pressure reading value over time. The cause for the pressure sensor being stuck at a pressure reading may be for a variety of reasons, such as hardware damage, ice frozen around the sensor, etc. Therefore, it is crucial to have a robust diagnosis algorithm to detect when a sensor failure in a fuel cell system is due to the sensor being stuck.

As stated above, when a pressure sensor is stuck the pressure feedback is flat for a certain period of time. In a fuel cell system, anode pressure feedback from an anode pressure sensor is used in anode pressure control, anode valve control, fuel cell system exhaust emission control, etc. A flat pressure sensor reading caused by a pressure sensor stuck failure does not reflect the true behavior of the fuel cell system, which causes other algorithms to not work properly. For example, during start up of the fuel cell system, if the anode pressure set point is set to 200 kPa and the anode pressure sensor is stuck at a constant pressure reading of 100 kPa, a controller of the fuel cell system will keep sending a maximum duty cycle command to an anode fuel injector to try to meet the pressure set point of 200 kPa. This will cause the anode pressure to rise, possibly above 700 kPa. Since the pressure reading is still 100 kPa, the system is not reflecting the true anode pressure. Eventually a shutdown diagnostic may detect that there is an issue and shutdown the fuel cell system. However, there is a need in the art for an algorithm that determines when an anode pressure sensor is stuck such that remedial actions may be taken before a shutdown diagnostic is triggered.

SUMMARY OF THE INVENTION

In accordance with the teachings of the present invention, a method for detecting an anode pressure sensor failure in a fuel cell system is disclosed. The system and method include a controller that sets an initial minimum anode pressure sensor value and an initial maximum anode pressure sensor value. The controller determines a desired time interval for sampling anode pressure measurements and determines a total number of samples of anode pressure measurements to be collected by the controller from an anode pressure sensor. The controller also compares a pressure difference between the initial or a measured minimum anode pressure and the initial or a measured maximum anode pressure to a predetermined pressure difference threshold and sets a pressure sensor fault if the pressure difference between the initial or measured minimum anode pressure and the initial or maximum anode pressure is less than the predetermined pressure difference threshold.

Additional features of the present invention will become apparent from the following description and appended claims, taken in conjunction with the accompanying drawings.

DETAILED DESCRIPTION OF THE EMBODIMENTS

The following discussion of the embodiments of the invention directed to a process for determining whether an anode pressure sensor in a fuel cell system is functioning properly is merely exemplary in nature and is in no way intended to limit the invention or its applications or uses.

Figure 1:
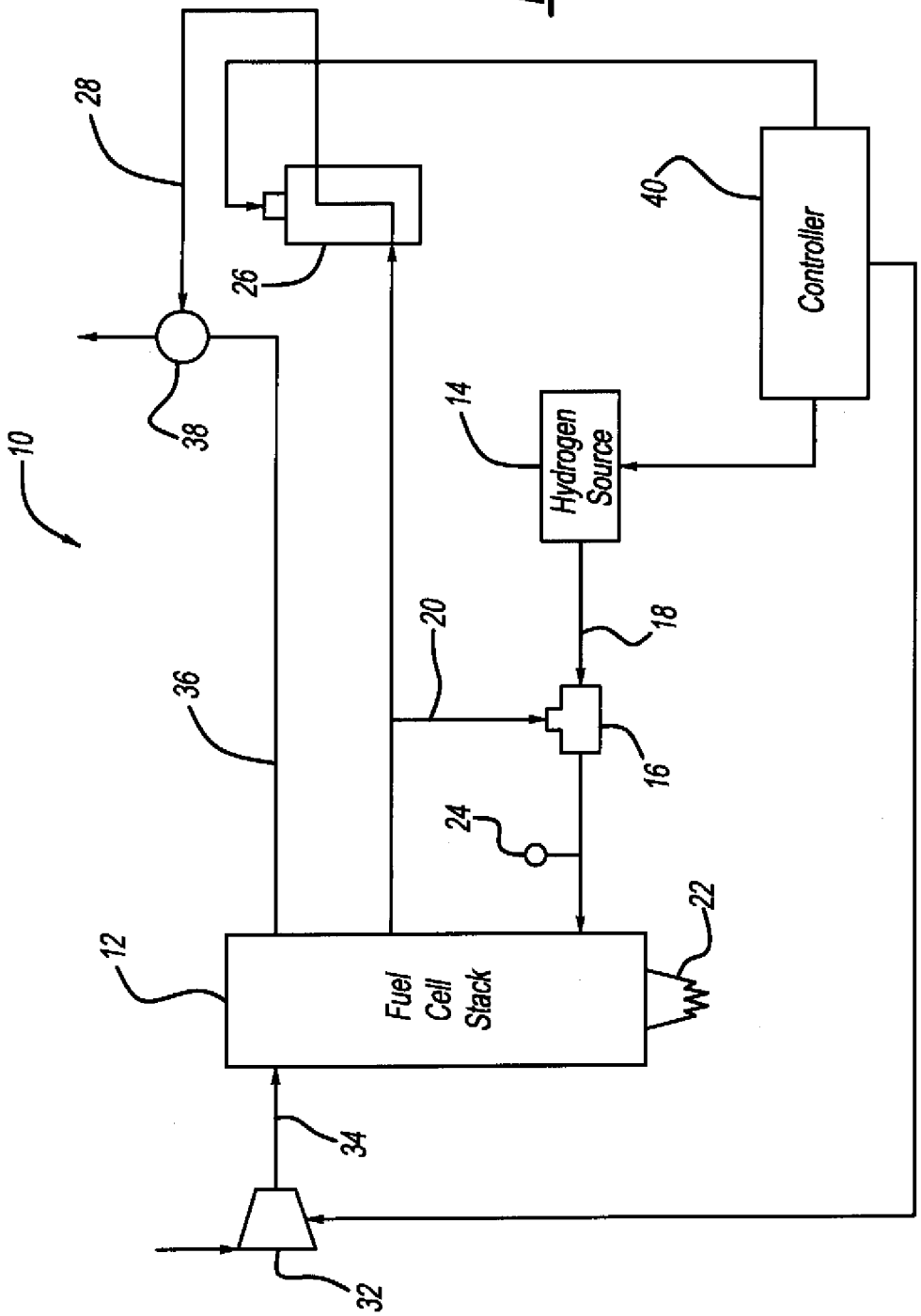
FIG. 1 is a schematic block diagram of a fuel cell system.

FIG. 1 is a schematic block diagram of a fuel cell system 10 including a fuel cell stack 12. The fuel cell system 10 is intended to generally represent any type of fuel cell system, such as fuel cell systems that re-circulate the anode exhaust gas back to the anode inlet and fuel cell systems that employ a split stack design with anode flow-shifting. A hydrogen source 14 provides fresh hydrogen to an anode side of the fuel cell stack 12 on anode input line 18 using an injector 16, such as an injector/ejector, as described in U.S. Pat. No. 7,320,840, "Combination of Injector-Ejector for Fuel Cell Systems," assigned to the assignee of this application and incorporated herein by reference. An anode exhaust gas is output from the stack 12 on an anode recirculation line 20, where it may be reintroduced into the fuel cell stack 12 using the injector 16. A pressure sensor 24 measures the pressure in the anode inlet line 18 in a position that is downstream of the anode recirculation line 20, such as at a location that is between the injector 16 and the fuel cell stack 12. An anode bleed valve 26 bleeds anode exhaust from the anode recirculation line, as discussed in more detail below.

The system 10 also includes a compressor 32 that provides cathode inlet airflow on cathode input line 34 to the stack 12. A cathode exhaust gas is output on a cathode exhaust gas line 36. The anode bleed valve 26 bleeds anode exhaust into the cathode output line 36 via a bleed line 28 and a mixing junction 38, thereby providing a path for anode exhaust gas to exit the fuel cell system 10, as is well known to those skilled in the art.

In order to provide current density measurements of the fuel cell stack 12, a current density measuring device 22 is provided. A controller 40 functions to operate the fuel cell system 10 and also detects the current density measurement signals from the current density measuring device 22 to determine a time interval for sampling the anode pressure measurement signals from the pressure sensor 24, as is discussed in more detail below.

As discussed above, if a pressure sensor in a fuel cell system fails or becomes stuck, the pressure feedback value may be flat for a period of time. The anode pressure feedback from the pressure sensor 24 is used in several fuel cell system control algorithms, for example, anode pressure control, anode valve control and exhaust emission control. A flat reading that does not accurately reflect the true pressure of the anode pressure sensor will cause other algorithms to not work properly as well. Thus, the algorithm discussed below is designed to provide a robust diagnosis algorithm to detect when an anode pressure sensor such as the anode pressure sensor 24 is not working properly.

Figure 2:
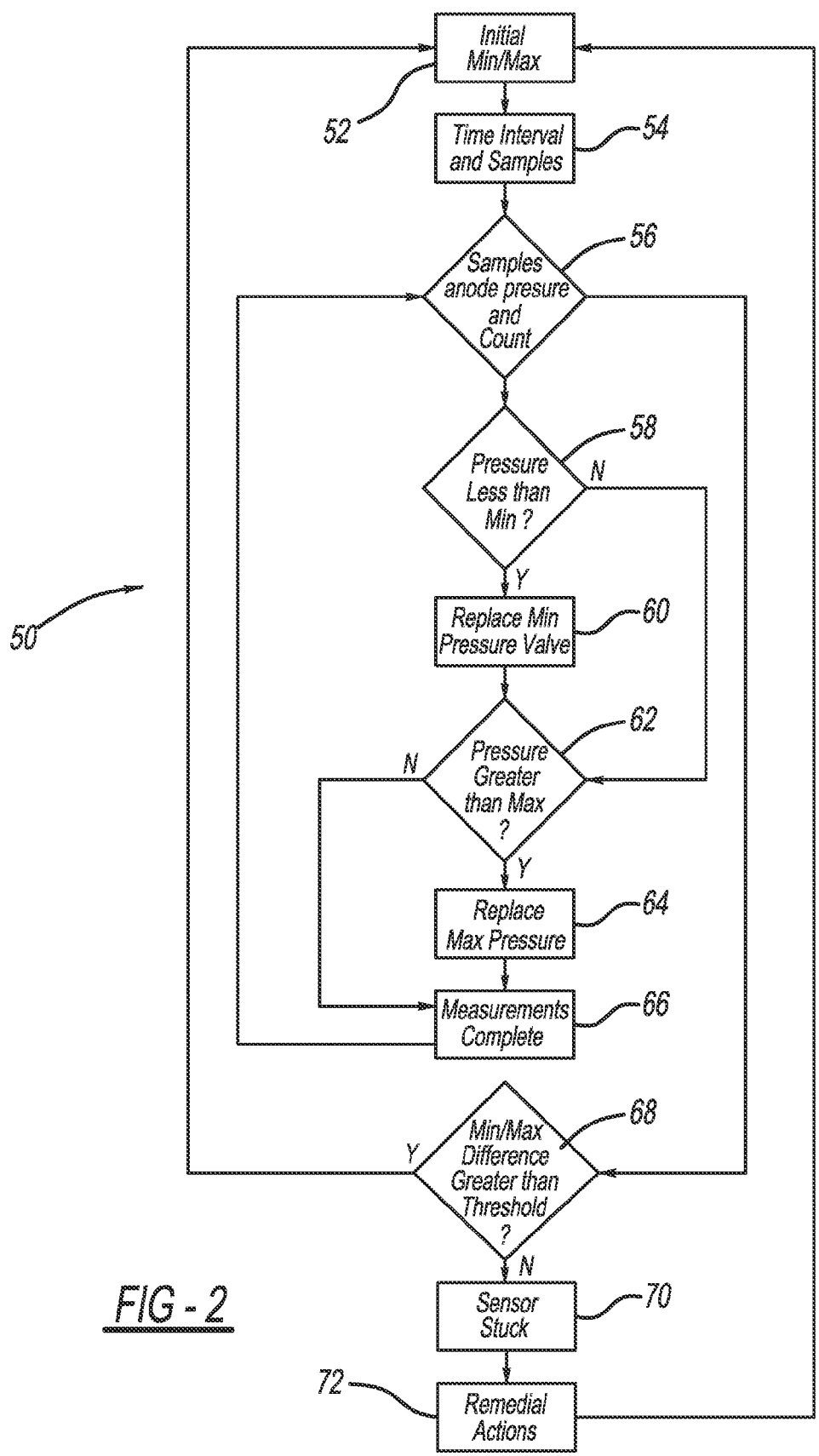
FIG. 2 is a flow diagram for an algorithm for determining whether an anode pressure sensor is functioning properly.

FIG. 2 is a flow diagram 50 for an algorithm that detects when an anode pressure sensor such as the anode pressure sensor 24 is not working properly. At box 52, an initial minimum anode pressure and an initial maximum anode pressure are set, and at box 54 a time interval and a desired total number of samples of anode pressure sensor measurements from the pressure sensor 24 are set. The time interval chosen at the box 54 is based on a calibratable table that uses fuel cell system factors such as current density from the current density measurement device 22 to determine the appropriate time interval. The total number of samples used may depend on stack operating conditions and the time interval that is determined using the calibratable table. The reason current density is used to determine the time interval during which the algorithm monitors anode pressure is because during high current density conditions anode pressure is expected to change faster, thus a shorter time interval between samples is more appropriate to execute the algorithm of the flow diagram 50 when the fuel cell stack 12 is operating at a high current density. What constitutes a high current density for the fuel cell stack 12 is dependent upon stack characteristics. For example, the current density of the fuel cell stack 12 during vehicle acceleration is likely to be at a high current density. In low current density conditions, such as when the fuel cell stack 12 is in idle mode, the anode pressure changes slowly. Thus a larger time interval is needed to detect a pressure stuck failure and to avoid false sensor stuck detection.

Once the initial minimum and maximum anode pressure are set at the box 52, and the time interval and number of samples are determined based on current density at the box 54, the algorithm begins to take samples of anode pressure measurements from the pressure sensor 24 to capture measured minimum and maximum pressure values. The initial minimum anode pressure and initial maximum anode pressure may depend on stack operating conditions such as, for example, the expected anode pressure for current operating conditions.

At decision diamond 56, anode pressure is sampled at a time interval as set at the box 54 and the sample number is counted, as discussed in more detail below. If, at decision diamond 58, a pressure reading from the anode pressure sensor 24 is determined to be less than the initial minimum pressure value set at the box 54, the algorithm will replace the initial minimum pressure value from the box 54 with the measured minimum pressure reading from the decision diamond 58 at box 60. If the pressure reading from the pressure sensor 24 at the decision diamond 58 does not drop below the initial minimum pressure value set at the box 54, the initial minimum pressure value from the box 54 is retained and the algorithm continues to decision diamond 62, where the algorithm determines whether the measured maximum pressure reading from the pressure sensor 24 is greater than the initial maximum pressure value set at the box 54. If the maximum measured anode pressure at the decision diamond 62 is greater than the initial maximum pressure set at the box 54, the measured maximum pressure sensor from the decision diamond 62 is used to replace the initial maximum pressure set at the box 54 at box 64. If the measured maximum pressure measured from the anode pressure sensor 24 at the decision diamond 62 is not greater than the initial maximum pressure set at the box 54, the algorithm continues to box 66 to determine that the anode pressure measurements for the sample is complete and returns to the decision diamond 56 to continue determining minimum and maximum anode pressure measurements for a next sample period if the total number of desired samples have not been achieved.

Once the desired number of samples have been measured for the determined time interval, as determined at decision diamond 56, the algorithm determines if the difference between the set minimum and maximum pressure values is greater than a variable predetermined threshold at decision diamond 68. The value for the predetermined pressure difference threshold between the minimum and maximum anode pressures depends on various stack operating parameters, such as current density and sensor resolution. The pressure difference threshold should at least be larger than the sensor resolution, otherwise the diagnostic will not be triggered.

If the difference between the set minimum and maximum pressure values is greater than the predetermined threshold, the algorithm of flow diagram 50 determines that the anode pressure sensor 24 is functioning properly and the algorithm returns to box 54 to repeat the process discussed above. If the algorithm determines that the difference between the minimum and maximum pressure set points is less than the predetermined pressure difference threshold at the decision diamond 68, a sensor stuck diagnostic is triggered at box 70 and one or more remedial actions are taken at box 72.

The sensor stuck diagnostic at the box 70 includes is a diagnostic that will be triggered if the algorithm determines that the difference between the minimum and maximum pressure set points is less than the predetermined pressure threshold for more than a predetermined number of pressure samples, which is a threshold to mature the diagnostic, for a predetermined number of total sample counts. The remedial actions taken at the box 72 may include commanding the anode pressure set-point to a predetermined value that does not include using measurements from the anode pressure sensor 24. For example, the anode pressure set-point may be set to 50 kPa above a cathode side pressure set point of the fuel cell stack 12 using open loop control, as is known to those skilled in the art. After evaluating the diagnostic of the algorithm of flow diagram 50, the algorithm resets the minimum and maximum pressure values and starts a new data capturing loop according to flow diagram 50 above.

Figure 3A:
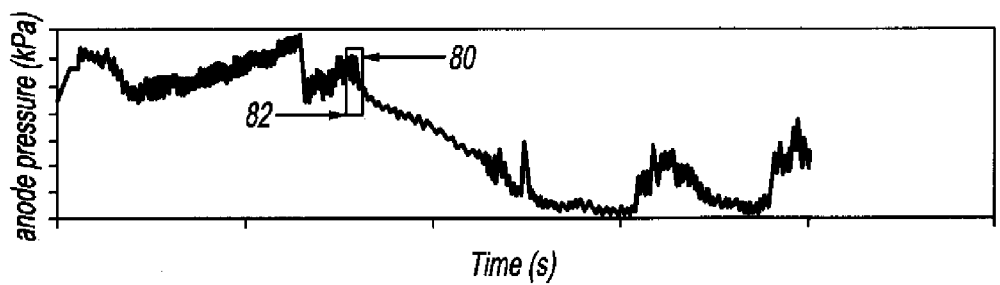
FIG. 3a is a graph with time on the horizontal axis and anode pressure in kPa on the vertical axis.

FIG. 3*a* shows a graph with time on the horizontal axis and anode pressure in kPa on the vertical axis. In this example, every 3 seconds the minimum and maximum anode pressures are extracted from the sampled data, with a 6 kPa pressure difference threshold to trigger the diagnostic. The minimum and the maximum anode pressure are extracted by a for-loop and if-then-else logic: during each sample loop, if the pressure value is smaller than the minimum pressure value captured in prior samples, this new pressure value will replace the minimum pressure value. If the pressure value is not smaller than the minimum pressure value captured in prior samples, the algorithm will retain the minimum pressure value. If the pressure value is larger than the maximum pressure value captured in prior sample, this new pressure value will replace the maximum pressure value, otherwise the algorithm will retain the maximum pressure value. As shown in FIG. 3*a*, the pressure maximum shown at reference numeral 80 and the pressure minimum shown at reference numeral 82 exceeds the 6 kPa pressure difference threshold, thus the sensor stuck diagnostic is not triggered during the entire time frame shown in FIG. 3*a*.

Figure 3B:
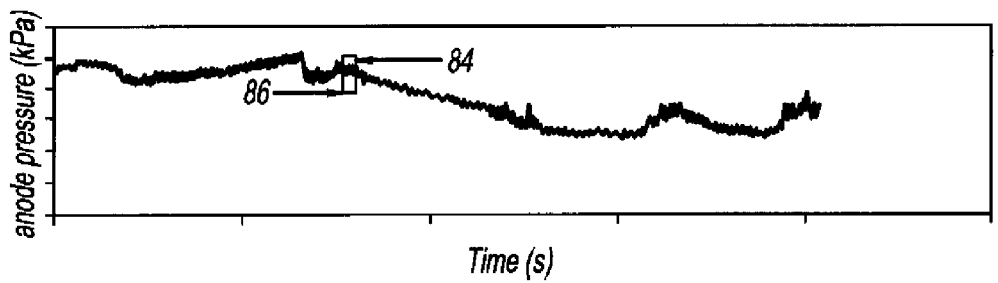
FIG. 3b is a graph with time on the horizontal axis and anode pressure in kPa on the vertical axis.

FIG. 3*b* shows a graph with time on the horizontal axis and anode pressure in kPa on the vertical axis. As with FIG. 3*a*, minimum and maximum anode pressures are extended every 3 seconds from the sample data and a 6 kPa pressure difference threshold is used to trigger the diagnostic. The graph of FIG. 3*b* is much flatter than the graph of FIG. 3*a*, thus the maximum pressure shown at reference numeral 84 and the minimum pressure shown at reference numeral 86, by way of example, do not exceed the pressure difference threshold of 6 kPa. Because at least one of the samples does not have a pressure difference that exceeds the threshold of 6 kPa, the sensor stuck diagnostic is triggered in FIG. 3*b*. Although the sensor stuck diagnostic is triggered in FIG. 3*b*, it may be caused by a false reading because the time interval chosen is too short or the pressure difference threshold is too large. The selection of the pressure difference threshold and the time interval is critical in accurately detecting a pressure sensor failure in the anode of the fuel cell stack 12. Thus, making both the pressure difference threshold and the chosen time interval tunable parameters helps the algorithm of flow diagram 50 to be more robust and to adapt to different fuel cell system operating conditions, thereby making false detection much less likely.

The foregoing discussion discloses and describes merely exemplary embodiments of the present invention. One skilled in the art will readily recognize from such discussion and from the accompanying drawings and claims that various changes, modifications and variations can be made therein without departing from the spirit and scope of the invention as defined in the following claims.

What is claimed is:

1. A method for detecting an anode pressure sensor failure in a fuel cell system comprising:
   using a controller to perform the steps of:
   setting an initial minimum anode pressure sensor value and an initial maximum anode pressure sensor value;
   determining a desired time interval for sampling anode pressure measurements and a total number of samples of anode pressure measurements to be collected by the controller from an anode pressure sensor;
   replacing the initial minimum anode pressure sensor value with a measured minimum anode pressure value if the measured minimum anode pressure is less than the initial minimum anode pressure;
   replacing the initial maximum anode pressure sensor value with a measured maximum anode pressure value if the measured maximum anode pressure is greater than the initial maximum anode pressure;
   comparing a pressure difference between the initial or replaced minimum anode pressure value and the initial or replaced maximum, anode pressure value to a predetermined pressure difference threshold; and
   setting a pressure sensor fault if the pressure difference between the initial or replaced minimum anode pressure and the initial or maximum anode pressure is less than the predetermined pressure difference threshold for a predetermined number of pressure samples.

2. The method according to claim 1 wherein the desired time interval for sampling anode pressure measurements is determined based on a calibratable table.

3. The method according to claim 2 wherein the calibratable table is based on fuel cell system factors that include fuel cell stack current density.

4. The method according to claim 3 wherein the desired time interval decreases when current density increases.

5. The method according to claim 4 wherein the desired time interval is approximately 3 seconds for high fuel cell stack current density.

6. The method according to claim 4 wherein the desired time interval is approximately 6 seconds for a low fuel cell stack current density.

7. The method according to claim 1 wherein the predetermined pressure difference threshold depends on the anode pressure sensor resolution.

8. The method according to claim 1 further comprising taking remedial actions if the pressure sensor fault occurs.

9. The method according to claim 8 wherein taking remedial actions includes setting an anode pressure set-point to a predetermined value above a cathode side pressure set-point using open loop control.

10. A method for detecting an anode pressure sensor failure in a fuel cell system comprising:
    using a controller to perform the steps of:
    setting an initial minimum anode pressure sensor value and an initial maximum anode pressure sensor value;

determining a desired time interval for sampling anode pressure measurements and determining a total number of samples of anode pressure measurements to be collected by the controller from an anode pressure sensor;

comparing a pressure difference between the initial or a measured minimum anode pressure and the initial or a measured maximum anode pressure to a predetermined pressure difference threshold; and setting a pressure sensor fault if the pressure difference between the initial or measured minimum anode pressure and the initial or maximum anode pressure is less than the predetermined pressure difference threshold for a predetermined number of samples.

11. The method according to claim 10 wherein the desired time interval for sampling anode pressure measurements is determined based on a calibratable table.

12. The method according to claim 11 wherein the calibratable table is based on fuel cell system factors that include fuel cell stack current density.

13. The method according to claim 12 wherein the desired time interval decreases when current density increases.

14. The method according to claim 10 wherein the predetermined pressure difference threshold depends on the anode pressure sensor resolution.

15. The method according to claim 10 further comprising taking remedial actions if the pressure sensor fault occurs.

16. A system for detecting an anode pressure sensor failure in a fuel cell comprising:

a fuel cell stack with an anode side and a cathode side;

an anode inlet line that introduces an anode gas into the fuel cell stack;

an anode recirculation line that recirculates anode exhaust gas into the anode inlet line;

an anode pressure sensor in the anode inlet line; and a controller programmed to detect failure of the anode pressure sensor, said controller programmed to set an initial minimum anode pressure sensor value and an initial maximum anode pressure sensor value, wherein the controller is further programmed to determine a desired time interval for sampling anode pressure measurements and a total number of samples of anode pressure measurements to be collected from the anode pressure sensor, said controller further programmed to compare a pressure difference between the initial or a measured minimum anode pressure value and the initial or a measured maximum anode pressure value to a predetermined pressure difference threshold and setting a pressure sensor fault if the pressure difference between the initial or measured minimum anode pressure and the initial or maximum anode pressure is less than the predetermined pressure difference threshold.

17. The system according to claim 16 wherein the desired time interval for sampling anode pressure measurements is determined based on a calibratable table that is based on fuel cell system factors that include fuel cell stack current density.

18. The system according to claim 17 wherein the desired time interval decreases when current density increases.

19. The system according to claim 16 wherein said controller is programmed to take remedial actions if the pressure sensor fault occurs.

20. The system according to claim 19 wherein the controller takes remedial actions by setting an anode pressure set-point to a predetermined value above a cathode side pressure set-point using open loop control.

* * * * *